(12) United States Patent
Morrison et al.

(10) Patent No.: US 6,634,749 B1
(45) Date of Patent: Oct. 21, 2003

(54) EYE TRACKING SYSTEM

(75) Inventors: Euan Morrison, Cambridgeshire (GB); Alan Edward Green, Cambridgeshire (GB); Nicholas Archibald Safford, Cambridgeshire (GB)

(73) Assignee: Leica Microsystems (Schweiz) AG, Heerbrugg (CH)

( * ) Notice: Subject to any disclaimer, the term of this patent is extended or adjusted under 35 U.S.C. 154(b) by 0 days.

(21) Appl. No.: 09/830,828

(22) PCT Filed: Nov. 2, 1999

(86) PCT No.: PCT/GB99/03625
§ 371 (c)(1),
(2), (4) Date: Sep. 12, 2001

(87) PCT Pub. No.: WO00/26713
PCT Pub. Date: May 11, 2000

(30) Foreign Application Priority Data

Nov. 2, 1998 (GB) .............................................. 9823977

(51) Int. Cl.⁷ .............................................. A61B 3/14
(52) U.S. Cl. ........................................ 351/209; 359/368
(58) Field of Search ................................. 351/205, 206, 351/208, 209, 210, 221; 359/368; 348/208.14; 382/103; 396/51

(56) References Cited

U.S. PATENT DOCUMENTS

| | | | | |
|---|---|---|---|---|
| 4,974,010 A | * | 11/1990 | Cleveland et al. | 351/210 |
| 5,016,282 A | * | 5/1991 | Tomono et al. | 382/117 |
| 5,231,674 A | * | 7/1993 | Cleveland et al. | 351/210 |
| 5,325,133 A | | 6/1994 | Adachi | 351/209 |
| 5,360,971 A | * | 11/1994 | Kaufman et al. | 250/221 |
| 5,526,089 A | | 6/1996 | Sato et al. | 354/410 |
| 5,552,854 A | | 9/1996 | Nishimura | 354/410 |
| 5,726,916 A | * | 3/1998 | Smyth | 351/210 |
| 5,818,954 A | * | 10/1998 | Tomono et al. | 382/115 |
| 5,867,308 A | | 2/1999 | Pensel et al. | 359/368 |
| 6,005,710 A | | 12/1999 | Pensel et al. | 359/379 |
| 6,307,526 B1 | * | 10/2001 | Mann | 345/8 |

FOREIGN PATENT DOCUMENTS

| | | |
|---|---|---|
| DE | 28 24 790 | 12/1978 |
| EP | 0 499 320 A1 | 8/1992 |
| EP | 0 572 979 A1 | 12/1993 |
| EP | 0 588 290 A3 | 3/1994 |
| EP | 0 588 431 A2 | 3/1994 |
| FR | 2 719 988 | 11/1995 |
| GB | 2 272 124 | 5/1994 |
| WO | WO81/02084 | 7/1981 |
| WO | WO89/02585 | 3/1989 |
| WO | WO96/13743 | 5/1996 |

OTHER PUBLICATIONS

J. Pensel et al., "Microscope, In Particular for Surgical Operations", Register Entry for EP0788613, Colum ns 13–16, (translated into English), pp 8–9 (Aug. 13, 1997).

* cited by examiner

*Primary Examiner*—Marvin M. Lateef
*Assistant Examiner*—John R. Sanders
(74) *Attorney, Agent, or Firm*—Hodgson Russ LLP (57) ABSTRACT

An optical instrument is provided for forming a viewable image of an object. The optical instrument includes an objective lens for forming the viewable image at an image plane, an eyepiece through which the user can view the viewable image, an eye sensor for sensing the direction of gaze of a user, and means for controlling a function of the optical instrument depending on the gaze direction. The eye sensor includes a light source for outputting light through the eyepiece towards the user's eye, a lens for causing the light from the source to be collimated when it exits the eyepiece, an imaging transducer for imaging the user's eye through the eyepiece and for generating an electrical image signal, and processing means for processing the image signal to determine the location of the user's pupil center and the location of a reflection of the light source to determine the gaze direction information.

36 Claims, 10 Drawing Sheets

EYE TRACKING SYSTEM

The present invention relates to an apparatus and method for tracking the direction of a user's gaze. The invention has particular relevance to an eye tracking system for use with optical instruments which form a viewable image of an object, such as microscopes, cameras, telescopes etc.

Leica Microsystems Limited has already proposed in WO96/13743 a microscope system which employs eye tracking techniques to track the position of gaze of a user viewing an image through a microscope eyepiece, which gaze information is used to control, for example, an auto-focus system. This is particularly useful at high magnification, where the depth of field is often limited and only a small part of the total field of view is in sharp focus at any one time. This earlier patent also teaches that the gaze information can be used to control other functions of the microscope, including hands-free movement of the microscope or the operation of a menu-driven computer system superimposed on the user's normal field of view.

There are many different techniques which can be used for eye tracking. The two most common of these are Limbus trackers and video eye trackers.

Limbus trackers usually operate by illuminating the user's eye, typically with one or more infra-red LEDs and detecting the light reflected off the white of the eye (sclera) using one or more photodetectors. Since the amount of light reflected off the white of the eye will vary depending on the position of the dark regions (the pupil and the iris), it is possible to determine where in the specified field of view the user is actually looking. However, this type of eye tracking system cannot unambiguously determine the angle of gaze because it only gives information relating to the position of the iris-sclera boundary. In addition, whilst Limbus tracking techniques give fairly good information on the horizontal position of the surface of the eye, they cannot accurately determine the vertical position due to obstruction from eyelashes and eyelids.

There are many different video-based eye tracking techniques. Some of these simply illuminate the eye and view the pupil using an imaging system. By determining the centre of the pupil from the image, information relating to the pointing direction of the eye can be obtained. This technique, however, suffers from the problem that movements of the observer's head cannot be distinguished from movements of the eye.

Other more sophisticated video-based eye tracking systems have been proposed which detect the position of the Purkinje images, which are the reflections of the illumination source off the surfaces of the cornea and the lens (often referred to as the highlights or glints). Whilst this technique is relatively accurate because it is independent of head movements, it suffers from the problem that some of the Purkinje images (those reflected off the eye lens) are extremely weak and therefore difficult to image clearly.

One aim of the present invention is to provide a different eye tracking technique for use with optical instruments which form a viewable image of an object, such as microscopes, cameras and the like.

According to one aspect, the present invention-provides an optical instrument for forming a viewable image of an object comprising: an objective lens for forming a viewable image of the object at an image plane; an eye sensor for sensing a direction of gaze of a user viewing the viewable image; and means for controlling a controllable function of the optical instrument in dependence upon the sensed direction of gaze; characterised in that the eye sensor comprises: (i) a light source for outputting light towards the user's eye; (ii) a lens associated with the light source for causing the light from said source to be substantially columnated when it hits the user's eye; (iii) an imaging transducer for imaging the front of the user's eye and for generating an electrical image signal of the front of the user's eye; and (iv) processing means for processing the electrical image signal from said imaging transducer to determine the location of the user's pupil centre and the location of a reflection of the light from said light source off the user's eye to determine therefrom the gaze information indicative of the direction of gaze of the user.

Preferably, one or more eyepieces are provided to facilitate the viewing of said viewable image. In a preferred form of the instrument, an additional illumination source is provided around the rim of an eyepiece for illuminating the surface of the user's eye in order to improve the quality of the eye image generated by the imaging transducer. Preferably a plurality of additional illumination sources are provided so that selected ones can be illuminated at any one time, and so that the generated images can be processed to remove the specular reflections of the additional light sources.

Exemplary embodiments of the present invention will now be described with reference to the accompanying drawings in which:

FIG. 6a schematically illustrates the form of an image output by the CCD sensor when a first set of illumination sources are switched on;

FIG. 6b schematically illustrates an image generated by the CCD sensor when a second set of illumination sources are switched on;

Figure 1:
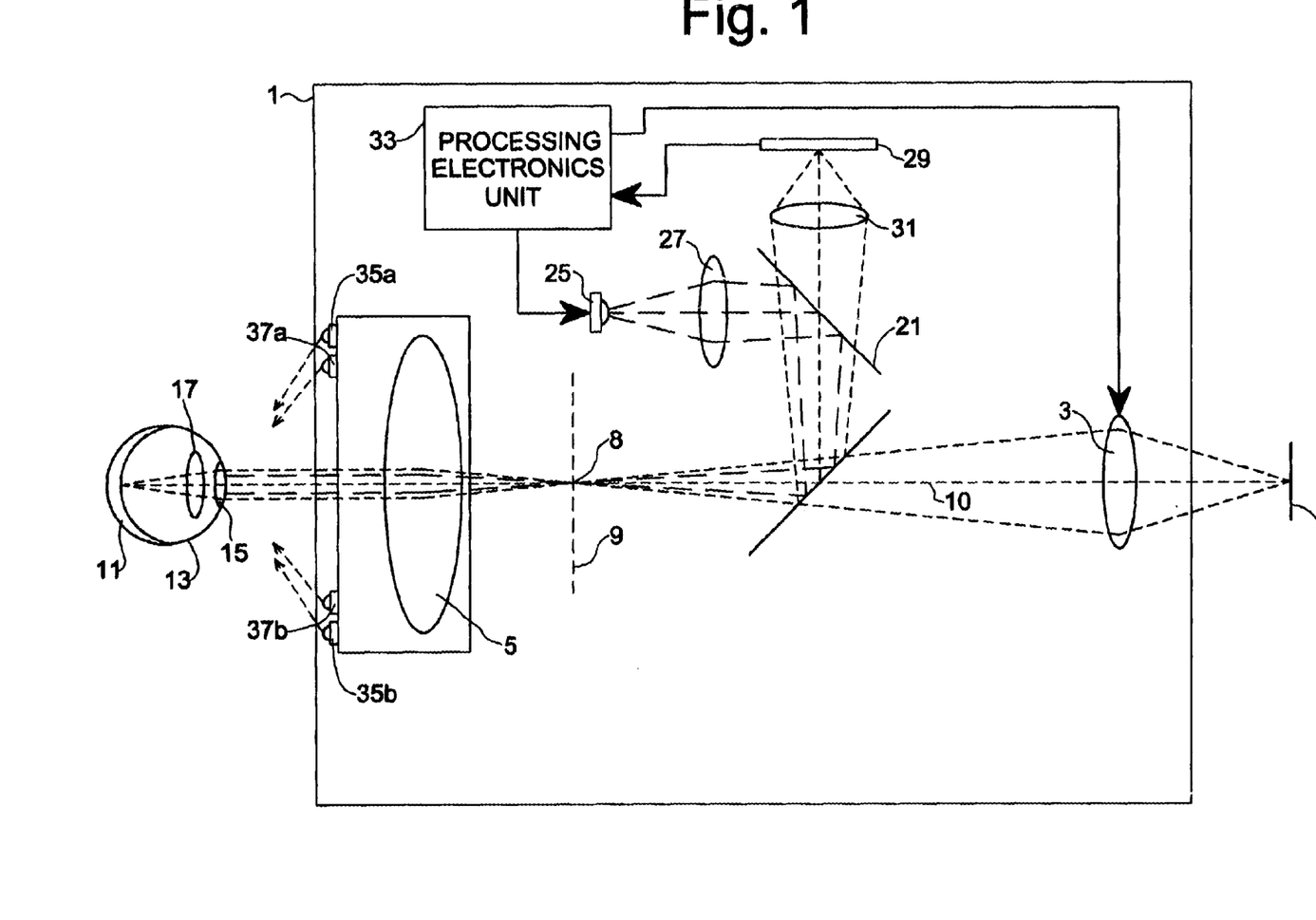
FIG. 1 is a schematic diagram illustrating the principal components of a surgical microscope embodying the present invention.

FIG. 1 is a schematic diagram of a surgical microscope 1. The microscope 1 comprises an objective lens 3 and an eyepiece 5, both of which are illustrated schematically by a single lens but which will, in practice, comprise a number of lenses. The objective lens 3 operates to generate an image of an object 7 being examined at an intermediate image plane (illustrated by the dashed line 9) which, in this embodiment is located at the focal plane of the eyepiece 5. As a result, the object 7 viewed by the observer appears to be at "infinity", i.e. the light from the object 7 emerges from the eyepiece 5 parallel to the optical axis 10 of the microscope. This image is then focussed by the cornea 15 and the eye lens 17 onto the retina 11 of the observer's eye 13.

As shown in FIG. 1, in this embodiment, the microscope 1 also comprises two beam splitters 21 and 23 both of which are optically located along the optical axis 10 of the microscope 1. Beam splitter 21 operates to reflect light from an illumination source 25 onto the cornea 15 of the observer's eye 13. A lens 27 is provided between the illumination source 25 and the beam splitter 21 for focussing the light from the source 25 substantially onto the focal point 8 of the eyepiece 5, resulting in the light from the source 25 which exits the eyepiece 5 being substantially parallel to the axis 10 of the microscope. Some of this illumination light will be reflected from the surface of the cornea 15 back through the eyepiece 5 towards the beam splitter 23, where it is reflected and focussed onto a CCD sensor 29 by lens 31. As shown in FIG. 1, the image generated by the CCD sensor 29 is input to a processing electronics unit 33, which is operable, in this embodiment, to process the received image to determine the observer's direction of gaze and to control the autofocussing of the objective lens 3 in response thereto.

In this embodiment, the system can identify the direction of gaze at a resolution of approximately ±3% of the full field of view of the microscope, which is around what would be expected for natural saccadic movements of the eye. This implies that the tracking technique itself has a resolution that is potentially better than this figure. In order to provide additional light for illuminating the user's eye, in this embodiment, separate light sources 35a and 35b and 37a and 37b are provided around the outer rim of the eyepiece 5. Preferably, the light sources 25, 35 and 37 emit near Infra Red (IR) light, since this is invisible to the user's eye and should not therefore, result in any reduction of the pupil size or in the quality of the image observed through the microscope. In this embodiment, these sources are provided by high powered 850 nm LED's which are operable to output about 0.2 mW at the front surface of the eye, which is well within current eye safety regulations.

Figure 2:
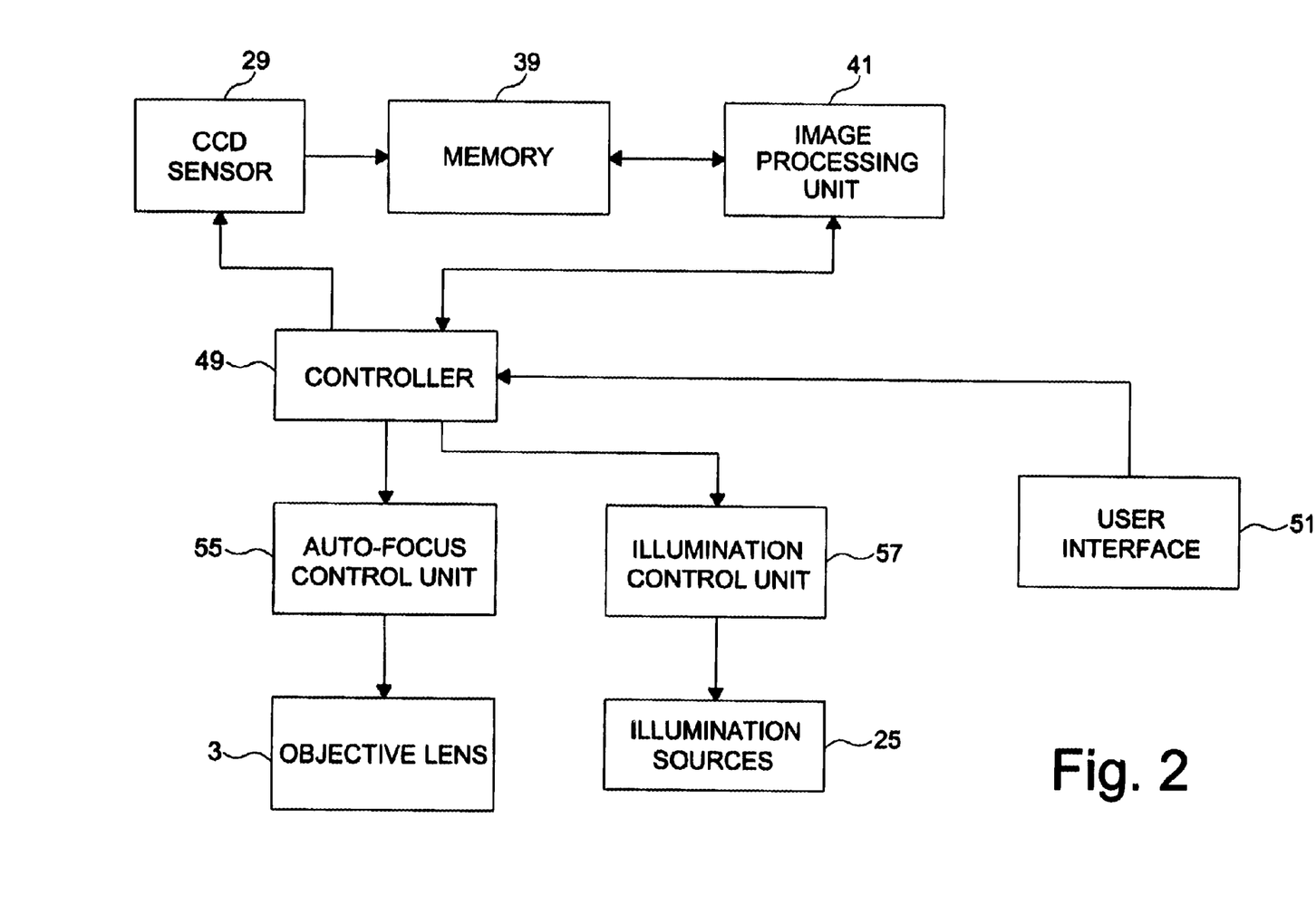
FIG. 2 is a block diagram illustrating the electronic components of the microscope shown in FIG. 1.

The way in which the system determines the observer's direction of gaze in this embodiment will now be described with reference to FIGS. 2 to 6. FIG. 2 is a block diagram illustrating the principal components of the eye tracking system used in the present embodiment to determine the observer's direction of gaze. As shown, the output image from the CCD camera 29 is supplied to a memory 39 where it is processed by an image processing unit 41 to determine the observer's direction of gaze. This is achieved by monitoring the position of the reflected image of the illumination source 25 relative to the centre of the observer's pupil.

Figure 3:
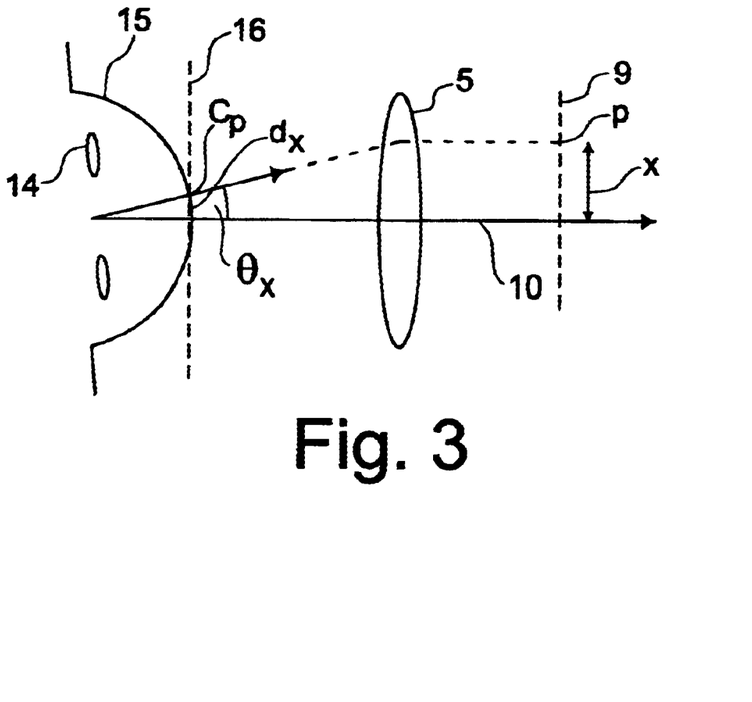
FIG. 3 is a schematic cross-sectional view of an observer's eye and the eyepiece illustrating the relationship between the direction of gaze and the optical axis of the microscope.

FIG. 3 schematically shows a cross section of the observer's eye showing the cornea 15, the iris 14, the eyepiece 5 and the intermediate image plane 9. As shown, the angle of gaze $\theta_x$ is related to the distance (x) between the optical axis 10 of the microscope 1 and the point (p) on the intermediate image plane 9 the observer is looking at. If the CCD camera 29 is focussed on the front surface of the observer's eye, i.e. at the plane 16, then the angle of gaze ($\theta_x$) will also be dependent upon the distance ($\delta_x$) between the point of intersection of the axis 10 of the microscope and the plane 16 and the observed centre of the observer's pupil ($c_p$). Consequently, there will be a linear relationship between $\delta_x$ and x. As those skilled in the art will appreciate, although FIG. 3 illustrates a cross section of the microscope in the x-z plane, a similar relationship exists for the angle of gaze ($\theta_y$) in the y-z plane. In this embodiment, in order to determine the relationship between $\delta_x$ and x and the relationship between $\delta_y$ and y, the system uses a calibration routine (which the observer can initiate via the user interface 51) in which the observer is asked to look at a plurality of known points on the field of view of the microscope and in which the CCD camera 29 captures images of the observer's eye when the observer is looking at each of those points. These points can be identified by providing a suitable calibration card which can be viewed by the microscope. By processing these images a scaling $A_x$ and an offset $O_x$ which relates $\delta_x$ to x and a scaling $A_y$ and an offset $O_y$ which relates $\delta_y$ to y, can be determined. These scalings and offsets are then stored for use when the microscope is in its normal mode of operation.

In the drawing shown in FIG. 3, the observer's eye is located on the optical axis of the microscope. However, as those skilled in the art will appreciate, since the light from the light source 25 exits the eyepiece 5 as a columnated beam, a similar relationship will exist if the observer's eye is off the axis of the microscope. Therefore, the system will be relatively insensitive to small head movements around the optical axis.

Figure 4:
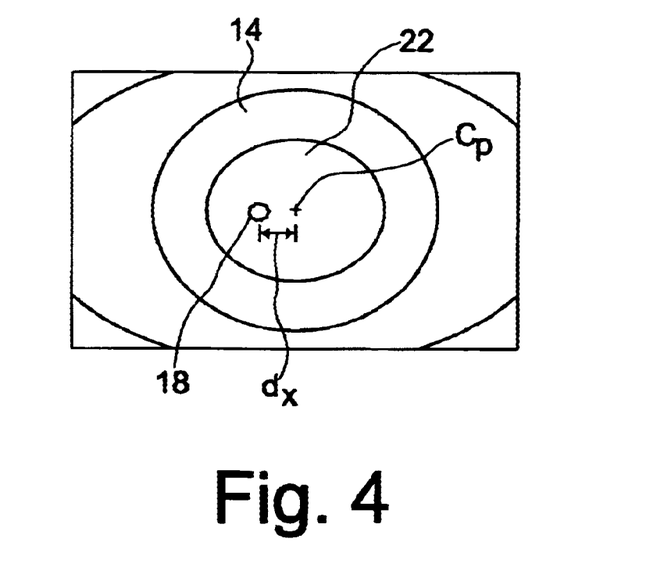
FIG. 4 is a schematic illustration of an image generated by a CCD sensor forming part of the electronic components shown in FIG. 2.

FIG. 4 schematically illustrates an example of the image generated by the CCD camera 29. As shown, the image shows the iris 14 and a reflection or highlight 18 of the illumination source 25 from the surface of the eye. FIG. 4 also illustrates the distance $\delta_x$ between 30 the highlight 18 and the centre of the pupil 22 at point $c_p$. As those skilled in the art will appreciate this distance can be determined by simple image processing techniques. Therefore, by capturing an image of the observer's eye and by measuring the distance $\delta_x$ and the corresponding distance $\delta_y$, the point (x,y) that the observer is looking at on the image plane 9 can be determined using the stored scalings and offsets. The inventors have established through experimentation and testing with various user's that this technique can determine the observer's angle of gaze within approximately ±3% of the full field of view of the microscope.

One of the main problems with this technique, however, is the generation of a clear image of the observer's eye using the CCD camera 29. Usually the light from the light source 25 is not enough to illuminate the entire surface of the observer's eye due to the losses in the beam splitters 21 and 23 and the eyepiece 5. Therefore, in this embodiment, separate illumination sources 35 and 37 are provided around the rim of the eyepiece 5 for illuminating the observer's eye. However, the light from these additional light sources introduce further reflections or highlights in the image generated by the CCD camera 29 which can make it difficult to determine the centre of the observer's pupil. The way in which this problem is overcome in this embodiment will now be described with reference to FIGS. 5 and 6.

Figure 5A:
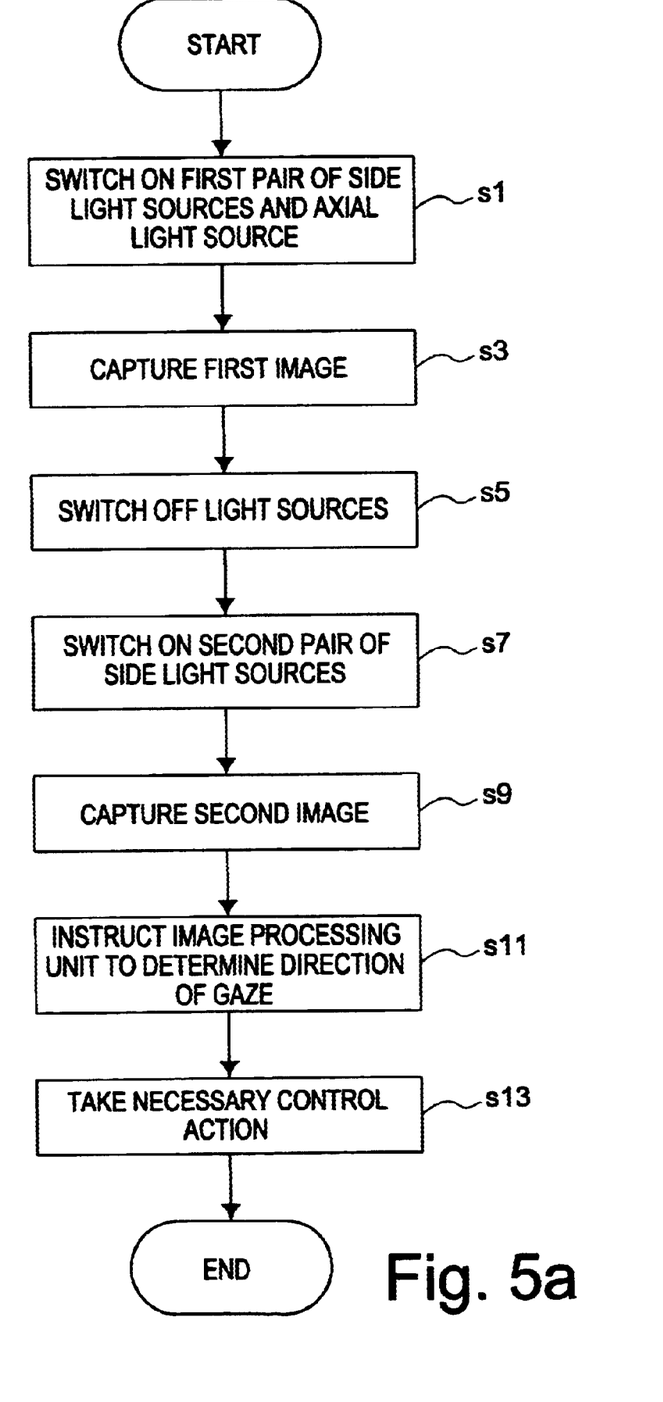
FIG. 5a is a flow diagram illustrating the control steps carried out by a controller which forms part of the electronic components shown in FIG. 2.
Figure 6A:
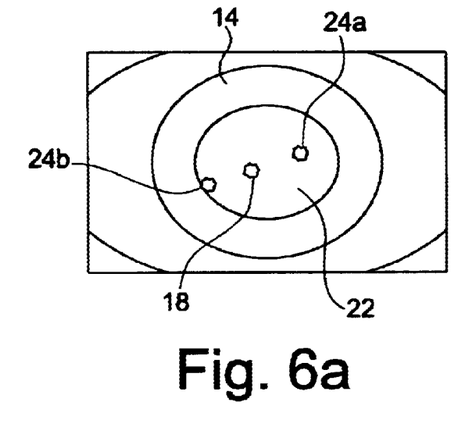
Figure 6B:
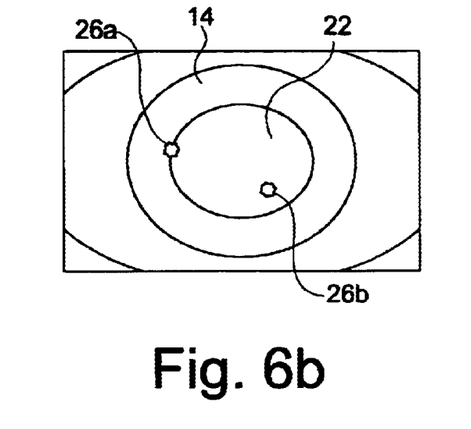

FIG. 5a is a flowchart illustrating the processing steps employed by the controller 49 shown in FIG. 2. As shown, in step S1, the controller 49 signals the illumination control unit 57 to turn on the light source 25 and a first pair of the side light sources 35a and 35b. The controller 49 then signals, in step S3, the CCD camera 29 to capture a first image of the observer's eye which is then stored in the memory 39. FIG. 6a illustrates the image generated by the CCD camera in this step. As shown, the image has three highlights—a central highlight 18 from the light source 25 and two outer highlights 24a and 24b generated by the light sources 35a and 35b respectively. The controller 49 then signals, in step S5, the illumination control unit 57 to switch off the light sources 25 and 35 and in step S7, to switch on the other pair of side illumination sources 37a and 37b. Then, in step S9, the controller 49 signals the CCD camera 29 to capture a second image of the observer's eye which is also then stored in memory 39. FIG. 6b schematically illustrates the resulting image captured by the CCD camera 29, which shows the outer highlights 26a and 26b generated from the illumination sources 37a and 37b respectively. The processing then proceeds to step S11 where the controller 49 instructs the image processing unit 41 to determine the observer's direction of gaze from the two stored images. Once the image processing unit 41 determines this gaze information, it passes it back to the controller 49 which, in step S13 takes the necessary control action. In this embodiment, this involves controlling the focus of the objective lens 3 using the auto-focus control unit 55.

Figure 5B:
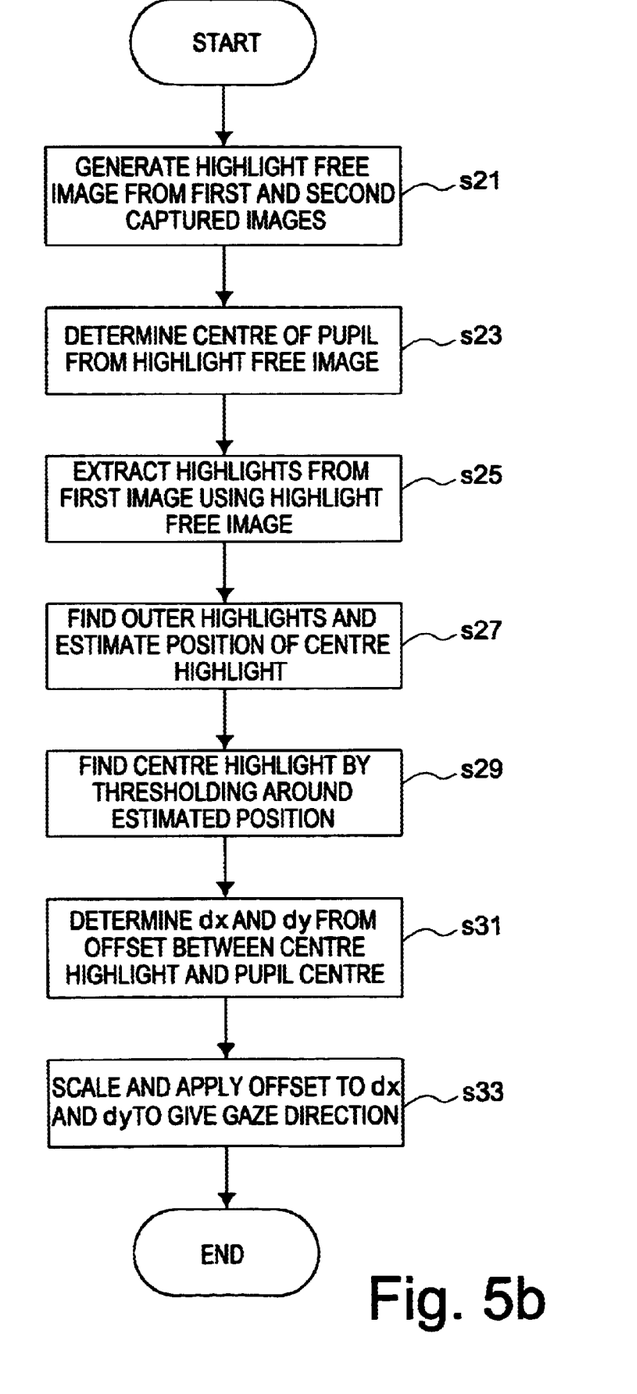
FIG. 5b is a flow chart illustrating the processing steps performed by an image processing unit which forms part of the electronic components shown in FIG. 2.
Figure 6C:
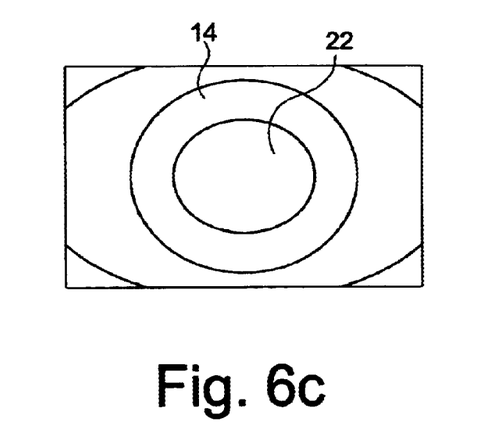
FIG. 6c schematically illustrates an image generated by combining and processing the images shown in FIGS. 6a and 6b.

FIG. 5b is a flow chart illustrating the processing steps employed by the image processing unit 31 to determine the observer's direction of gaze. As shown, in step S21, the image processing unit 41 generates a highlight free image from the first and second images stored in memory 39 (images shown in FIGS. 6a and 6b), by taking the lower of the pixel values from the two images, at each pixel. This highlight free image is shown in FIG. 6c. This technique works since the highlights 18, 24 and 26 appear at different pixel locations in the two images and since the pupil is much darker than the highlights, the pixel values of the highlights will be much larger. The processing then proceeds to step S23 where the image processing unit 41 determines the centre of the pupil 22 from the highlight free image. It does this, in this embodiment, by thresholding the image to identify the boundary between the pupil 22 and the iris 14. A best fit circle is then fitted to the identified boundary and the centre of this circle is identified as being the pupil centre.

The processing then proceeds to step S25 where the image processing unit extracts the highlights 18, 24a and 24b from the first image by subtracting the highlight free image shown in FIG. 6c from the image shown in FIG. 6a (i.e. subtracting the pixel values of the image shown in FIG. 6c from the pixel values of the image shown in FIG. 6a). The processing then proceeds to step S27 where the image processing unit determines the position of the outer highlights 24a and 24b by thresholding the image generated in step S25. From the determined position of the outer highlights 24, the image processing unit 41 estimates the position of the centre highlight 18. It can do this, since the illumination source 25 (which generates the centre highlight 18) and the illumination sources 35a and 35b (which generate the outer highlights 24) are in a known fixed position relative to each other. In this embodiment, the illumination sources 35a and 35b are diametrically opposite each other on the outer rim of the eyepiece 5 and illumination source 25 is effectively on the optical axis of the microscope. Therefore, the position is estimated to be halfway between the two outer highlights. The processing then proceeds to step S29 where the image processing unit 41 determines a more accurate position of the centre highlight 18 by thresholding the image around the estimated position. The image processing unit 41 then determines, in step S31, δx and δy from the determined positions of the centre highlight 18 and the pupil centre. Finally, in step S33, the image processing unit scales δx and δy by using the stored scalings $A_x$ and $A_y$ and applies the appropriate offsets $O_x$ and $O_y$ to give the gaze direction in terms of the x,y co-ordinate of the point in the field of view 9 that the observer is looking at. In this embodiment, in order to track the observer's eye, the above processing steps are performed at approximately 25 times per second.

As those skilled in the art will appreciate, the above described eye tracking technique works well in this microscope application because the observer's eye is usually located, in use, at approximately the same position relative to the eyepiece 5. This technique is also particularly appropriate for use in microscopes and other optical instruments in which the observer is viewing an image that appears essentially at infinity, since the x,y position on the image plane where the observer is looking is simply determined by the angle of gaze. Further, if the image is genuinely at infinity, then small head movements will have no effect on the observer's angle of gaze.

In principal, information relating to the angle of gaze of the observer can be obtained by measuring the difference in the position of the pupil centre with respect to any of the highlights produced from any of the illumination sources. However, by using a highlight generated by a source (source 25) that is also effectively at infinity provides much more accurate results. There are two main reasons for this. Firstly, the highlight is produced near the centre of the corneal bulge, where the radius of curvature of the cornea is relatively constant. As a result, the relatively large variations in curvature of the cornea that occur near the transition point from the corneal bulge to the rest of the eyeball have little effect on the measurement. This is not the case for the pairs of highlights produced by the light sources which are attached, to the outer rim of the eyepiece 5, since these highlights appear very close to this transition region. Secondly, small head movements have little effect on the relative position of the source to the eye. As a result, there is no need to factor in any additional correction to take into account the relative change in the source from the eye as the head moves. Again, this would not be the case if the highlights produced by the light sources around the rim of the eyepiece were used, since the sources of illumination are relatively close to the observer's eye.

Alternative Embodiments

A number of modifications and alternative embodiments will now be described with reference to FIGS. 7 to 10.

Figure 7:
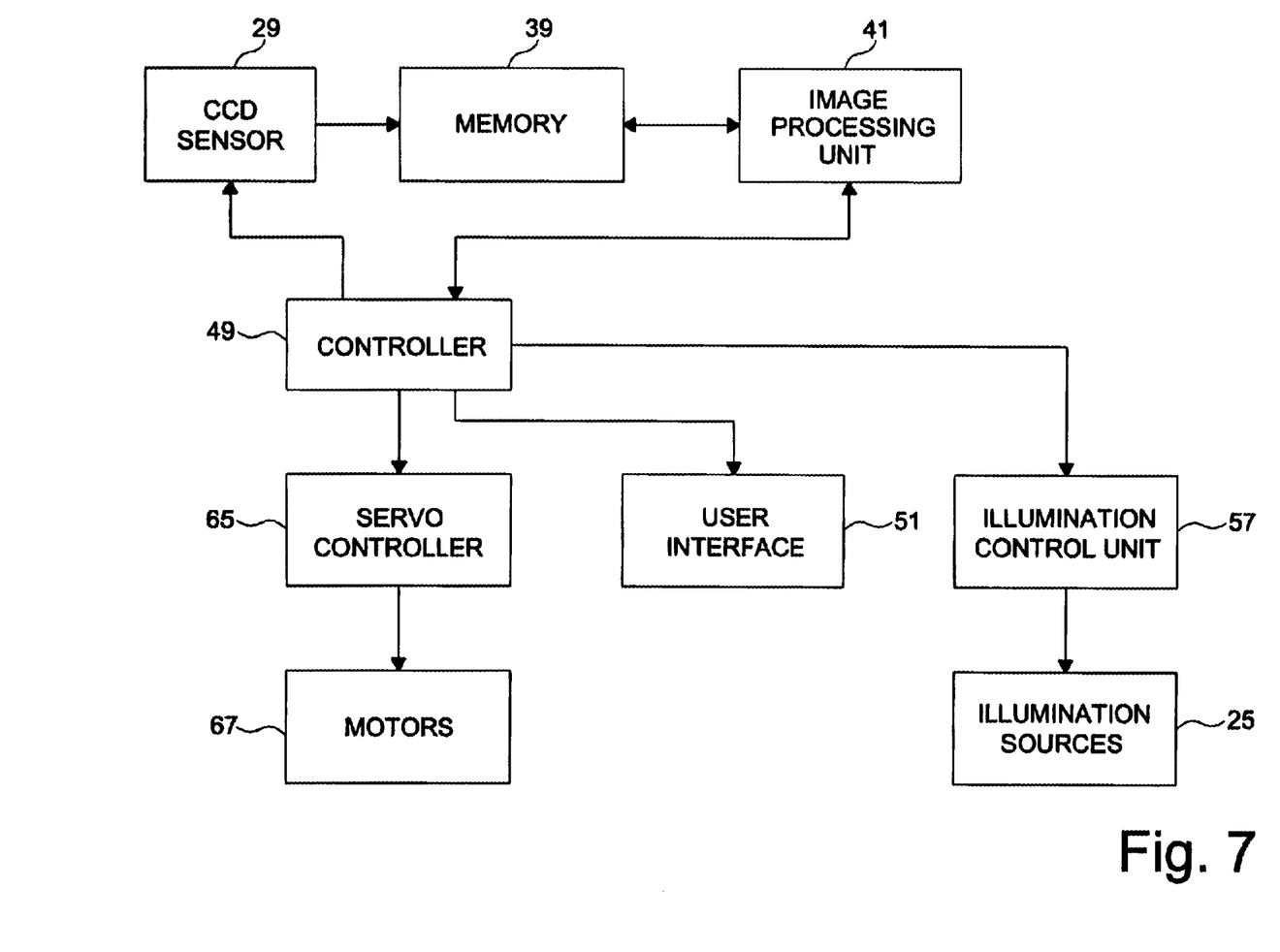
FIG. 7 is a block diagram illustrating the electronic components of an optical instrument embodying the present invention.

In the above embodiment, the direction of gaze information was used to control the automatic focussing of the microscope 1. As those skilled in the art will appreciate, the direction of gaze information can be used for other purposes. FIG. 7 shows the processing blocks used in an embodiment where the gaze information is used to control the movement of the microscope 1. Processing blocks which are the same as those described with reference to FIG. 2 have the same reference numeral. As shown, the only difference in this embodiment is the provision of a servo-controller 65 which is operable to receive the gaze information output by the controller 49 and in response thereto, is operable to control the operation of a number of motors 67 which move the microscope over the object 7 being viewed.

Figure 8:
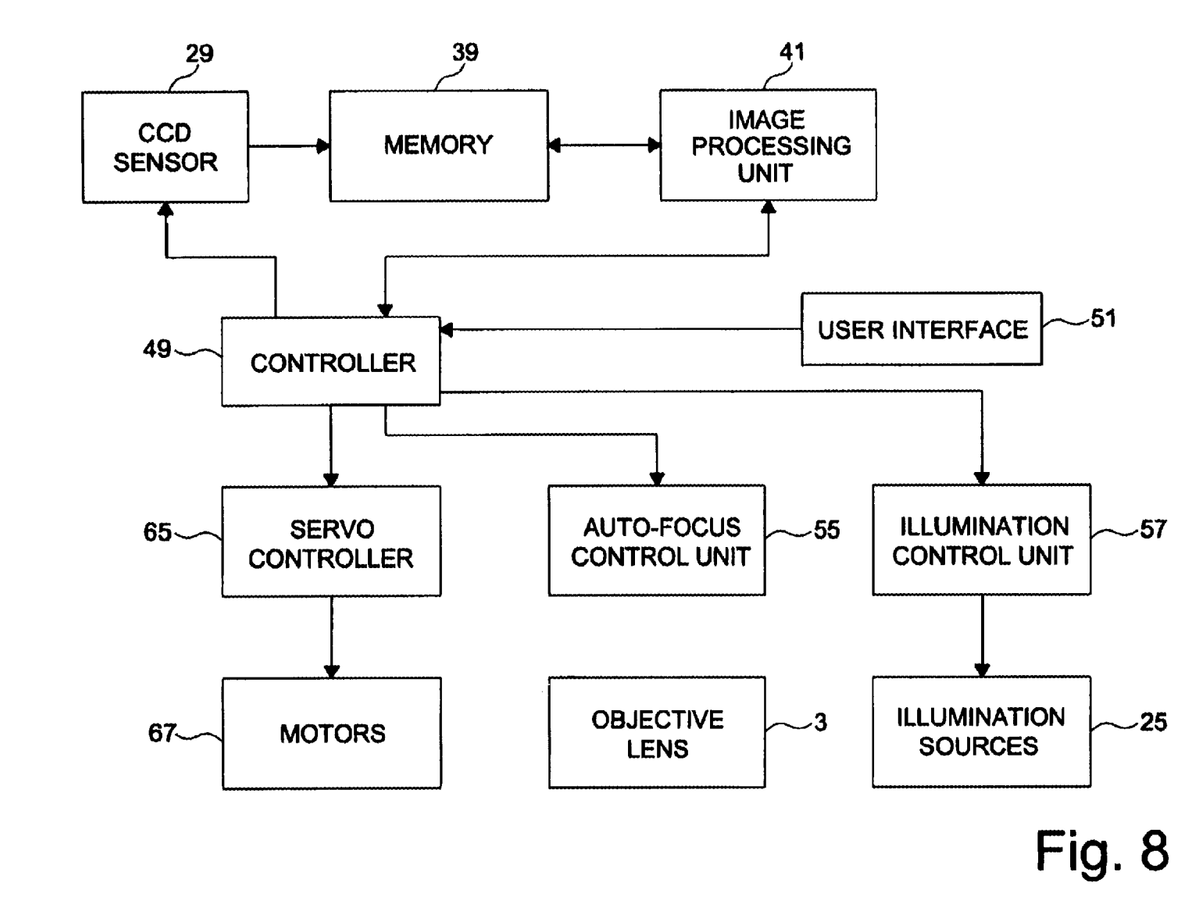
FIG. 8 is a block diagram illustrating the electronic components of an optical instrument embodying the present invention.

FIG. 8 shows the form of the processing and control electronics used in a further embodiment of the invention. As shown in FIG. 8, in this embodiment, the determined direction of gaze information is used to control the positioning of the microscope and the focussing of the objective lens 3.

Figure 9:
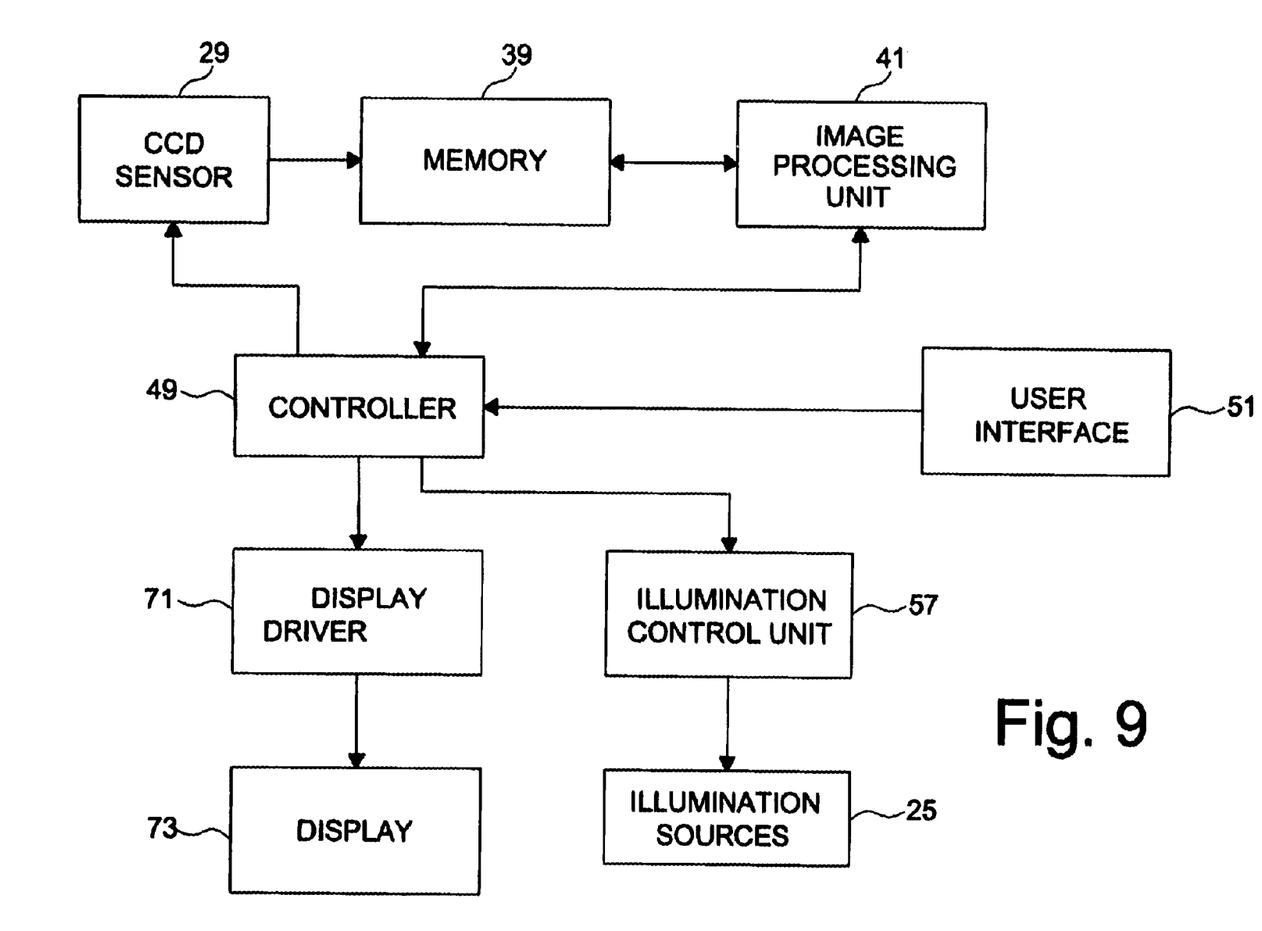
FIG. 9 is a block diagram illustrating the electronic components of an optical instrument embodying the present invention.

FIG. 9 shows the processing and control blocks used in yet another embodiment of the present invention. As shown, in this embodiment, the direction of gaze information obtained by the controller is passed to a display driver 71 which controls the display of menus on a display 73 which is located within the viewfinder of the microscope.

In the above embodiment, the CCD camera 29 was focussed onto the plane 16 shown in FIG. 3. Provided the depth of field of the CCD camera is relatively large, the observer's eye does not have to be exactly at the plane 16 for the observer's eye to be in focus. In an alternative embodiment, the CCD camera 29 may have an associated autofocussing circuitry which operates to automatically focus the CCD camera onto the front surface of the observer's eye. In such an embodiment, however, the lens system for the CCD camera would either have to be telecentric or the calibration data would have to be adapted in dependence upon the current focus point of the CCD camera. This can be done, for example, by making the observer look at the calibration points for various different distances from the eyepiece 5, in order to determine the relationship between the calibration data and the focus point of the CCD camera.

In the above embodiment, two pairs of side illumination sources 35 and 37 were provided on the outer rim of the eyepiece 5, for illuminating the observer's eye. As those skilled in the art will appreciate, illumination of the observer's eye can be achieved through the use of a single illumination source on the rim of the eyepiece. However, this is not preferred, since illumination from a single source does not provide uniform illumination of the observer's eye. Further, by providing at least two side light sources on the rim of the eyepiece, the glints from these sources in the image can be removed by combining the images generated when only one of the side lights is switched on at any one time.

Figure 10:
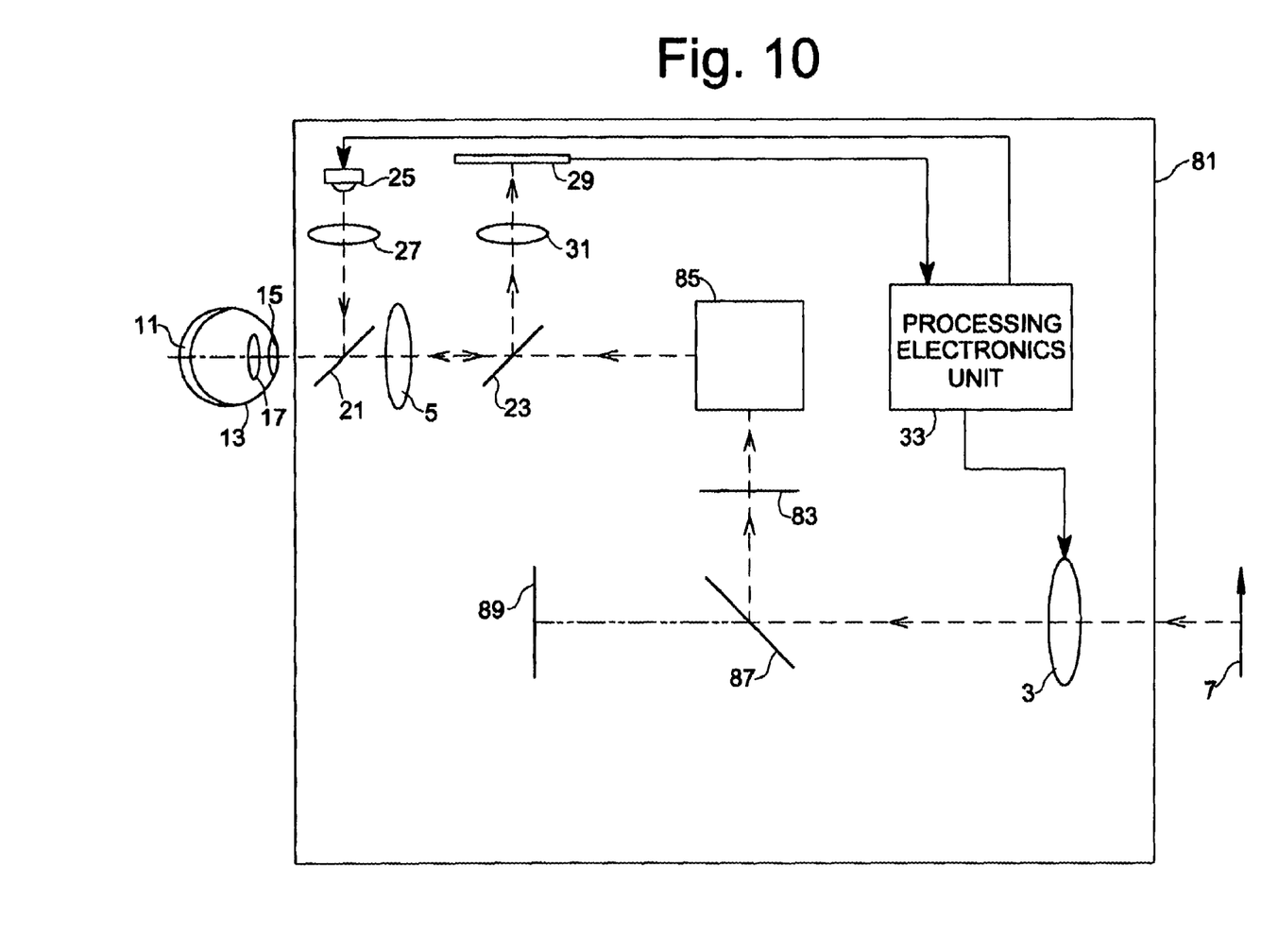
FIG. 10 is a schematic diagram of a camera embodying the present invention.

The above embodiments have all related to an eye tracking technique for use in an optical microscope. As those skilled in the art will appreciate, the eye tracking technique described above can be used in many other optical instruments, such as cameras, telescopes etc. FIG. 10 shows a schematic diagram of a camera 81 which employs the eye tracking technique discussed above. As shown, the camera 81 comprises an objective lens 3 for focussing the object onto the intermediate image plane. However, in a camera, a real image is generated at the intermediate image plane by locating a diffusing screen 83 at the intermediate plane. The real image formed on the diffusing screen 83 is then viewed by the observer through the eyepiece 5 and a prism 85 which operates to reorientate the image the right way up. The camera 81 also has a mirror 87 which can be moved up or down so that the light from the object can be focussed onto the film 89. The remaining components of the eye tracking system are the same as those used in the microscope embodiments described above and will not, therefore, be described again. It should, however, be noted that, in this embodiment, the CCD sensor 29 and lens 31 are located in front of the diffusing screen 83, because the eye image cannot pass through the diffusing screen 83.

In the above embodiment, calibration data was stored for each observer. In an alternative embodiment, the calibration data of one observer could be used for one or more other observers. However, such an embodiment is not preferred since the results will not be as accurate for the other observers. This is because the calibration data for an observer is dependent upon the radius of curvature of the observer's corneal bulge. The accuracy of such common calibration data may be improved if it is obtained by averaging several observer's calibration data.

In the above embodiments, the system automatically changed the focus of the objective lens if the observer's direction of gaze moved to a position in the field of view which was out of focus. In some applications, such an automatic change of the focus may not be desired. In this case, the processing electronics may be arranged so that the automatic focussing only changes either if the user remains focussed at the same point for a predetermined length of time or if the observer inputs a control command signalling that he wishes the focus to be changed.

In the above embodiments, a beam splitter was used to effectively place the CCD sensor and the sensor lens on the axis of the microscope. As those skilled in the art will appreciate, it is not essential to use such a beam splitter. For example, the CCD sensor and the sensor lens can be located off the optical axis 10 of the microscope, provided the CCD sensor can still "see" the observer's eye. Alternatively still, if the CCD sensor is relatively small compared to the diameter of the objective lens, then the CCD sensor can be placed along the axis 10 of the objective lens. However, this embodiment is not preferred because it reduces the amount of light entering the observer's eye. Similarly, the illumination source 25 may be located off the optical axis 10 of the microscope, provided the light from it will hit the observer's eye and be reflected back into the microscope and onto the CCD sensor.

In the above embodiments, a single optical path has been illustrated through the optical instruments. As those skilled in the art will appreciate, where there are two optical paths (one for each eye) a similar eye tracking system could be provided in the other optical path. Alternatively, if the optical instrument allows the observer to view the object with both eyes, then a single selectable eye tracking system could be provided.

Many other embodiments will be apparent to those skilled in the art. The above embodiments and modifications have been given by way of example only and, as those skilled in the art will appreciate, the modifications made to some of the embodiments will be applicable to the other embodiments.

What is claimed is:

1. An optical instrument for forming a viewable image of an object, comprising:

an objective lens for forming a viewable image of the object at an image plane;

an eyepiece through which a user can view said viewable image at said image plane;

an eye sensor for sensing a direction of gaze of a user viewing the viewable image through said eyepiece; and     means for adjusting a controllable function of said optical instrument in dependence upon the sensed direction of gaze;

characterised in that said eye sensor comprises:

(i) a light source for outputting light through said eyepiece towards the user's eye;

(ii) a lens associated with said light source for causing the light from said source to be substantially collimated when it exits said eyepiece towards said user's eye;

(iii) an imaging transducer for imaging the front of the user's eye through said eyepiece and for generating an electrical image signal of the front of the user's eye; and         (iv) processing means for processing the electrical image signal from said imaging transducer to determine the distance between the location, within the image, of the user's pupil centre and the location, within the image, of a reflection of the light from said light source off the user's eye, and to determine said gaze information using said distance and predetermined calibration data which defines a relationship between said distance and the point on the image plane the user is currently looking at.

2. The instrument according to claim 1, wherein said eyepiece comprises a lens system for increasing the apparent field of view of the optical instrument.

3. The instrument according to claim 2, wherein said lens associated with said light source is operable to focus the light from said light source substantially at the focal point of said eyepiece lens system.

4. The instrument according to claim 2, wherein said objective lens is operable to form said viewable image at an image plane which is located substantially at the focal point of said eyepiece lens system.

5. The instrument according to claim 1, wherein said imaging transducer is located off the optical axis of said optical instrument.

6. The instrument according to claim 5, further comprising a beam splitter for reflecting the light reflected from the front of the user's eye onto said imaging transducer.

7. The instrument according to claim 1, wherein said imaging transducer comprises a CCD sensor.

8. The instrument according to claim 7, wherein said CCD sensor comprises a 2D CCD sensor.

9. The instrument according to claim 7, wherein said imaging transducer further comprises a lens for focussing the light from the user's eye onto said CCD sensor.

10. The instrument according to claim 9, wherein said imaging transducer lens is operable to focus at a plane located at a predetermined distance in front of said eyepiece.

11. The instrument according to claim 9, wherein said imaging transducer further comprises autofocus means for automatically focussing said imaging transducer lens on the front surface of said user's eye.

12. The instrument according to claim 11, comprising means for varying said calibration data in dependence upon a current focal point of said imaging transducer lens.

13. The instrument according to claim 1, further comprising one or more further light sources for illuminating the user's eye.

14. The instrument according to claim 13, wherein said one or more further light sources are located around an outer rim of said eyepiece.

15. The instrument according to claim 14, wherein two pairs of additional light sources are provided around said rim.

16. The apparatus according to claim 1, wherein said light source is operable to generate near infra-red light.

17. The instrument according to claim 16, wherein said light source comprises an 850 nm LED.

18. The instrument according to claim 1, wherein said processing means is operable to determine said pupil centre by thresholding the image to locate the boundary between the pupil and the iris and by identifying the centre of the circle which best fits the located boundary.

19. The instrument according to claim 1, wherein said calibration data is generated in advance during a calibration routine in which the user looks at different preselected locations on the image plane and in which the processing means is operable to correlate the determined distances between pupil center and light source reflection from the corresponding electrical image signals with the preselected locations.

20. The instrument according to claim 1, wherein said calibration data comprises a scaling factor for scaling said distance between said two locations.

21. The instrument according to claim 20, wherein said calibration data comprises a scaling factor for an x component of said distance and a scaling factor for a y component of said distance.

22. The instrument according to claim 21, wherein said calibration data further comprises an offset for an x direction and an offset for a y direction.

23. The instrument according to claim 1, wherein at least two further light sources are provided for illuminating the user's eye and wherein the instrument further comprises illumination control means for selectively illuminating different ones of said at least two further light sources and wherein said imaging transducer is operable to generate an image of the user's eye when different ones of said at least two further light sources are illuminated and is operable to generate a highlight-free image by combining the images output from said transducer when the different light sources are illuminated.

24. The instrument according to claim 23, wherein said processing means is operable to determine the centre of said pupil from said highlight-free image.

25. The instrument according to claim 23, wherein said illumination control means is operable to illuminate a first pair of said at least two further light sources during a first time interval and is operable to illuminate a second different pair of said at least two further light sources during a second time interval and wherein said imaging transducer is operable to generate an image of the user's eye during said first time interval and during said second time interval.

26. The instrument according to claim 25, wherein said illumination control means is operable to switch on said light source for outputting light through said eyepiece during said first time interval and wherein said processing means is operable to determine the location of said reflection of said light from said light source by locating reflections from said first pair of further light sources, estimating a position of said reflection of said light from said light source based on said reflection locations from said first pair of further light sources, and thresholding the image around said estimated position.

27. The apparatus according to claim 1, wherein said light source for outputting light through said eyepiece is located off the axis of said optical instrument.

28. The instrument according to claim 27, further comprising a beam splitter located on the optical axis of the instrument for reflecting the light from said source onto the user's eye.

29. The instrument according to claim 1, wherein said imaging transducer is operable to output an image signal a plurality of times per second and wherein said processing means is operable to determine repeatedly said gaze information from said images.

30. The instrument according to claim 29, wherein said imaging transducer is operable to output an image signal between ten and fifty times per second.

31. The instrument according to claim 1, wherein said controllable function is automatic focussing of the objective lens so that the point in the field of view which the user is looking at is in focus.

32. The instrument according to claim 1, wherein said controllable function is movement of the optical instrument over the object being viewed.

33. The instrument according to claim 1, wherein said controllable function is content of a display which is optically superimposed on the field of view of the instrument.

34. The instrument according to claim 1, which is a microscope.

35. The instrument according to claim 1, which is a camera.

36. A method of operating an optical instrument for forming a viewable image of an object, comprising the steps of:

providing an objective lens for forming a viewable image of the object at an image plane;

viewing the viewable image through an eyepiece;

sensing a direction of gaze of a user viewing the image; and controlling a controllable function of the optical instrument in dependence upon the sensed direction of gaze;

characterised in that said sensing step comprises the steps of:
  (i) using a light source to output light through said eyepiece towards the user's eye;
  (ii) providing a lens associated with said light source for causing the light from said source to be substantially collimated when it exits said eyepiece towards said user's eye;
  (iii) providing an imaging transducer for imaging the front of the user's eye through said eyepiece for generating an electrical image signal of the front of the user's eye; and
  (iv) processing the electrical image signal from said imaging transducer to determine the distance between the location, within the image of the user's pupil centre and the location, within the image, of a reflection of the light from said light source off the user's eye and to determine said gaze information using said distance and predetermined calibration data which defines a relationship between said distance and the point on the image plane the user is currently looking at.

* * * * *